US00PP25456P2

(12) United States Plant Patent
Schnupper

(10) Patent No.: US PP25,456 P2
(45) Date of Patent: Apr. 21, 2015

(54) ***CHAMAECYPARIS* PLANT NAMED 'SUNNY SMILE'**

(50) Latin Name: *Chamaecyparis lawsoniana*
Varietal Denomination: Sunny Smile

(71) Applicant: Frank Schnupper, Westerstede (DE)

(72) Inventor: Frank Schnupper, Westerstede (DE)

( * ) Notice: Subject to any disclaimer, the term of this patent is extended or adjusted under 35 U.S.C. 154(b) by 33 days.

(21) Appl. No.: 13/987,041

(22) Filed: Jun. 27, 2013

(51) Int. Cl.
*A01H 7/00* (2006.01)

(52) U.S. Cl.
USPC ..... Plt./213

(58) Field of Classification Search
CPC ..... A01H 7/00
USPC ..... Plt./213
See application file for complete search history.

(56) References Cited

PUBLICATIONS

Van Nliet, New Plants <http://www.newplants.nl/en/planten/c/chamaecyparis-lawsoniana-sunny-smile/>, retrieved from the internet Sep. 23, 2014.*

* cited by examiner

*Primary Examiner* — June Hwu
*Assistant Examiner* — Keith Robinson
(74) *Attorney, Agent, or Firm* — Penny J. Aguirre

(57) ABSTRACT

A new cultivar of *Chamaecyparis* named 'Sunny Smile' that is characterized by its foliage that is yellow-green and creamy white in color and its narrow and upright plant habit.

2 Drawing Sheets

Botanical classification: *Chamaecyparis lawsoniana.*
Varietal denomination: 'Sunny Smile'.

BACKGROUND OF THE INVENTION

The present invention relates to a new and distinct cultivar of *Chamaecyparis lawsoniana* and will be referred to hereafter by its cultivar name, 'Sunny Smile'. 'Sunny Smile' represents a new evergreen coniferous tree grown for landscape use.

'Sunny Smile' was discovered by the Inventor as a chance seedling in a trial garden in Westerstede, Germany in summer of 2004. The exact parentage is unknown, however it is most likely a seedling of open pollinated 'Stardust' (not patented) based on its characteristics and its proximity to 'Stardust' in the garden.

Asexual propagation of the new cultivar was first accomplished by softwood stem cuttings by the Inventor in Westerstede, Germany in August of 2008. Asexual propagation by softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Sunny Smile', as a unique cultivar of *Chamaecyparis.*

1. 'Sunny Smile' exhibits foliage that is yellow-green and creamy white in color.
2. 'Sunny Smile' exhibits a moderately narrow and upright plant habit.

The probable parent plant, 'Stardust', differs from 'Sunny Smile' in having foliage that is deep yellow in color. 'Sunny Smile' can be compared to the cultivars 'Ivonne' (not patented) and 'Stewartii' (not patented). Both are similar to 'Sunny Smile' in having a yellow coloration to their foliage. 'Ivonne' differs from 'Sunny Smile' in having foliage that is deep yellow in color. 'Stewartii' differs from 'Sunny Smile' in having foliage that is deep yellow in color and in having a broader plant habit.

BRIEF DESCRIPTION OF THE DRAWINGS

The accompanying colored photographs illustrate the overall appearance and distinct characteristics of the new *Chamaecyparis*. The photographs were taken of a three year-old plant as grown in a 19-cm container in Stroe, The Netherlands.

The photograph in FIG. 1 provides an overall view of the plant habit of 'Sunny Smile'.

Figure 1:
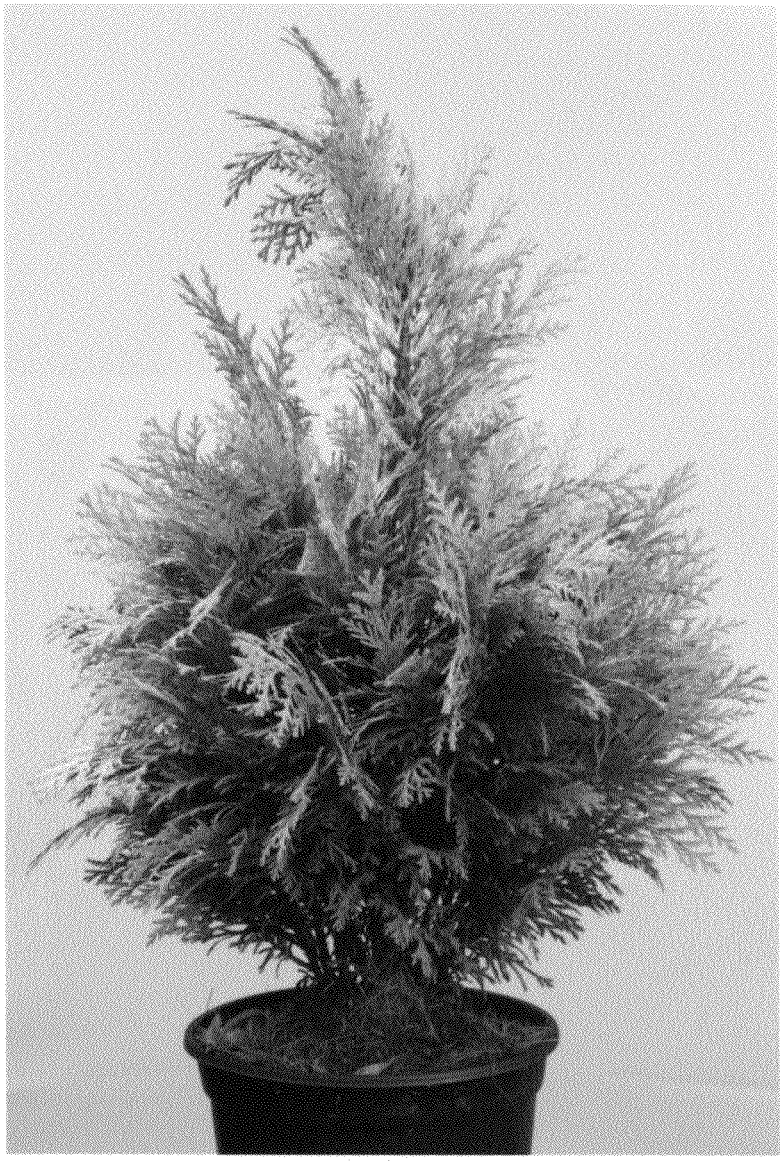
Figure 2:
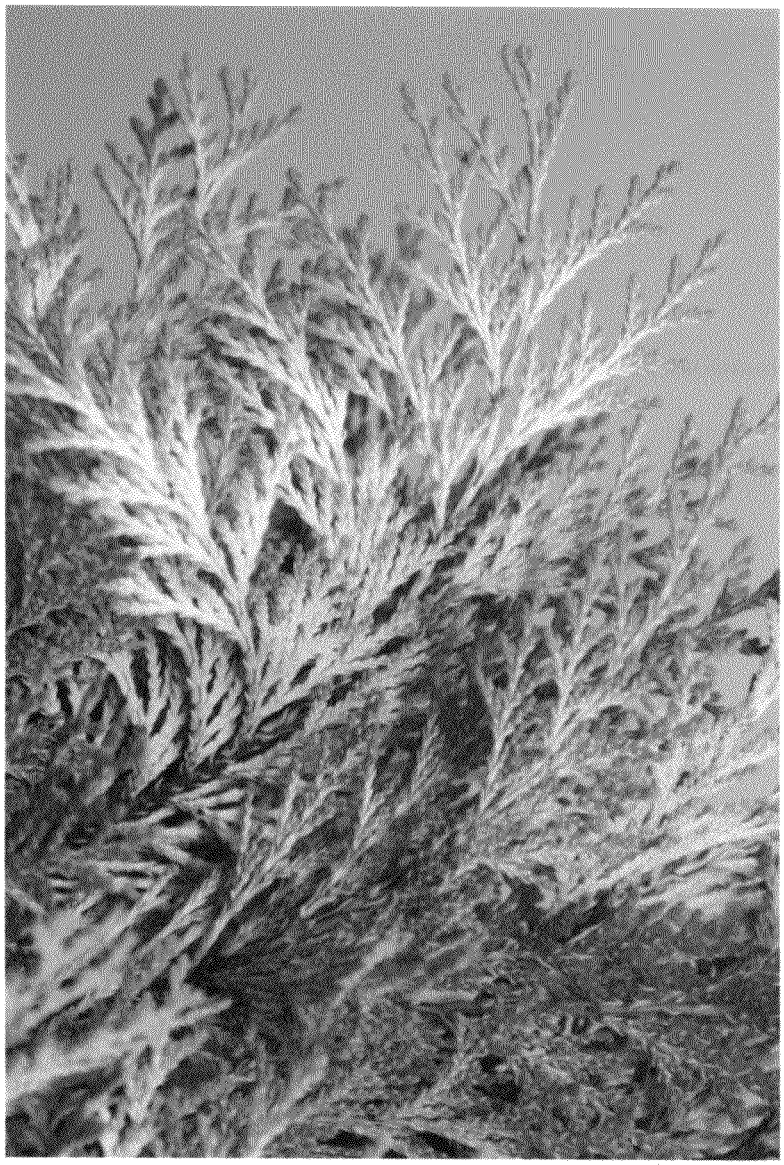

The photograph in FIG. 2 provides a close-up view of the new foliage of 'Sunny Smile'.

The colors in the photographs are as close as possible with the photographic and printing technology utilized and the values cited in the detailed botanical description accurately describe the colors of the new cultivar.

DETAILED BOTANICAL DESCRIPTION

The following is a detailed description of three year-old plants of the new cultivar as grown in 19-cm containers in Stroe, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Perennial shrub (conifer).

*Growth habit.*—Upright.

*Height and spread.*—An average of 52.8 cm in height and 34.3 cm in spread as a three year-old plant.

*Cold hardiness.*—At least in U.S.D.A. Zone 6.

*Diseases and pests.*—No studies have been done to establish any resistance or susceptibility to any specific diseases or pests, however no pest or disease problems have been observed.

*Root description.*—Fibrous and well-branched.

*Growth rate.*—Moderate.

*Propagation.*—Softwood stem cuttings.

*Root development.*—Roots initiate in 3 to 4 weeks and will fully develop in a 11-cm container in about 24 months.

Branch description:

*Branching.*—Very freely branching, about 9 basal branches, 66 lateral branches, and numerous branchlets (sprays) per lateral branch.

*Branch surface* (*texture*).—All branches covered with scale-like leaves, slightly glossy and smooth with bark at base of basal branches scaled but bark-like.

*Branch shape.*—Rounded.

*Branch size.*—Basal branches; Up to 50 cm in length and an average of 4 mm in diameter, lateral branches; 21.9 cm in length and 3 mm in diameter, branchlets; average of 6 mm in length and 2 mm in diameter (with spray about 7 mm in width).

*Internode length.*—6 mm in length for lateral branches and 3 mm in length for branchlets.

*Branch color.*—One-year old branches and lateral branches are 150D in color, older bark at base of basal stems is N199B in color, young branchlets are 145C in color.

*Branch strength.*—Basal and lateral branches are very strong with branchlets moderately strong.

Foliage description:

*Leaf arrangement.*—Opposite.

*Leaf shape.*—Scale-like, linear.

*Leaf division.*—Simple.

*Leaf base.*—Cuneate.

*Leaf apex.*—Apiculate.

*Leaf venation.*—Not visible.

*Leaf margins.*—Entire.

*Leaf surface.*—Both surfaces smooth and moderately glossy.

*Leaf color.*—Young upper side; 144C, young lower side; 144B to 144C, mature upper side; 150D, mature lower side; 145A, and changing to 150C to 150D.

*Leaf fragrance.*—Strong fragrance typical for *Chamaecyparis lawsoniana* when crushed due to very small glands on the bases of the scales; narrow and elliptic in shape, an average length of 0.75 mm, average diameter 0.5 mm, 145A in color.

*Leaf size.*—An average of 3.5 mm in length and 1.5 mm in width.

*Leaf quantity.*—Over 10,000 scale-like leaves.

*Durability to stresses.*—Very high.

Cone description: No cones have been produced to date.

It is claimed:

1. A new and distinct cultivar of *Chamaecyparis* plant named 'Sunny Smile' as herein illustrated and described.

* * * * *